(12) United States Patent
Mizutani et al.

(10) Patent No.: US 9,598,668 B2
(45) Date of Patent: Mar. 21, 2017

(54) TEMPERATURE-RESPONSIVE CELL CULTURE SUBSTRATE AND METHOD FOR PRODUCING THE SAME

(75) Inventors: Manabu Mizutani, Tokyo (JP); Hiroya Watanabe, Tokyo (JP); Yuriko Kitano, Tokyo (JP)

(73) Assignee: CELLSEED INC., Tokyo (JP)

( * ) Notice: Subject to any disclaimer, the term of this patent is extended or adjusted under 35 U.S.C. 154(b) by 1312 days.

(21) Appl. No.: 13/124,298

(22) PCT Filed: Oct. 14, 2009

(86) PCT No.: PCT/JP2009/067774
§ 371 (c)(1),
(2), (4) Date: Jun. 2, 2011

(87) PCT Pub. No.: WO2010/044417
PCT Pub. Date: Apr. 22, 2010

(65) Prior Publication Data
US 2011/0229962 A1    Sep. 22, 2011

(30) Foreign Application Priority Data

Oct. 14, 2008 (JP) ................................ 2008-288220

(51) Int. Cl.
| | |
|---|---|
| C12M 3/00 | (2006.01) |
| C12N 5/00 | (2006.01) |
| B29C 59/16 | (2006.01) |
| C08J 7/18 | (2006.01) |
| C12M 1/22 | (2006.01) |
| C12M 1/00 | (2006.01) |
| C12M 1/12 | (2006.01) |
| C12M 1/26 | (2006.01) |
| B29C 35/08 | (2006.01) |
| B29K 25/00 | (2006.01) |

(52) U.S. Cl.
CPC ............ *C12N 5/0068* (2013.01); *B29C 59/16* (2013.01); *C08J 7/18* (2013.01); *C12M 23/10* (2013.01); *C12M 23/20* (2013.01); *C12M 25/06* (2013.01); *C12M 33/00* (2013.01); *B29C 2035/0877* (2013.01); *B29K 2025/00* (2013.01); *C08J 2325/06* (2013.01); *C08J 2433/26* (2013.01); *C12N 2533/30* (2013.01)

(58) Field of Classification Search
CPC ....................................................... B29C 59/16
USPC .......................................................... 436/85
See application file for complete search history.

(56) References Cited

U.S. PATENT DOCUMENTS

| | | | |
|---|---|---|---|
| 5,202,227 A | 4/1993 | Matsuda et al. | |
| 5,284,766 A | 2/1994 | Okano et al. | |
| 5,593,814 A | 1/1997 | Matsuda et al. | |
| 6,956,077 B1 | 10/2005 | Akiyama et al. | |
| 7,470,424 B2 | 12/2008 | Kataoka et al. | |
| 7,691,369 B2 | 4/2010 | Kataoka et al. | |
| 2003/0036196 A1 | 2/2003 | Okano et al. | |
| 2004/0009566 A1 | 1/2004 | Okano et al. | |
| 2004/0028657 A1 | 2/2004 | Okano et al. | |
| 2004/0197907 A1 | 10/2004 | Kataoka et al. | |
| 2006/0234377 A1 | 10/2006 | Okano et al. | |
| 2006/0240400 A1 | 10/2006 | Yamato et al. | |
| 2006/0240552 A1 | 10/2006 | Yamato et al. | |
| 2007/0015277 A1 | 1/2007 | Hattori et al. | |
| 2007/0148137 A1 | 6/2007 | Okano et al. | |
| 2008/0118474 A1 | 5/2008 | Okano et al. | |
| 2008/0131476 A1 | 6/2008 | Kanzaki et al. | |
| 2008/0215073 A1 | 9/2008 | Iwanaga et al. | |
| 2008/0226692 A1 | 9/2008 | Sato et al. | |
| 2008/0227203 A1 | 9/2008 | Watanabe et al. | |
| 2008/0289052 A1 | 11/2008 | Okano et al. | |
| 2009/0011504 A1 | 1/2009 | Kataoka et al. | |
| 2011/0229962 A1 | 9/2011 | Mizutani et al. | |
| 2012/0052524 A1 | 3/2012 | Kinooka et al. | |
| 2012/0107930 A1 | 5/2012 | Sasaki et al. | |
| 2012/0156781 A1 | 6/2012 | Takahashi et al. | |

(Continued)

FOREIGN PATENT DOCUMENTS

| | | |
|---|---|---|
| EP | 0402718 | 12/1990 |
| EP | 1961809 | 8/2008 |

(Continued)

OTHER PUBLICATIONS

Kwon et al. "Accelerated cell sheet recovery by cografting of PEG with PIPAAm onto porous cell culture membranes", Biomaterials, 2003,24:1223-1232.*
Akiyama et al. "Ultrathin Poly(N-isopropylacrylamide) grafted layer on polystyrene surfaces for cell adhesion/detachment control", Langmuir, 2004, 20:5506-5511.*
Itoga et al. "Saibo sheet kogaku: Pattern-ka saibo sheet no sakusei to riyo" Jpn. J. Clin. Med., vol. 66, No. 5, pp. 887-891 (May 2008).
Tsuda et al. "Micro pattern-ka saibo ni yoru sanjigen soshiki no sakusei" Nano Gakkai Dai 5 Kai Taikai Koen Yokoshu, p. 260 (May 2007).

(Continued)

*Primary Examiner* — Bin Shen
(74) *Attorney, Agent, or Firm* — Nixon & Vanderhye PC (57) ABSTRACT

A substrate having a pattern of two or more materials exhibiting different grafting efficiencies for a temperature-responsive polymer that varies its interaction with water in a temperature range of 0 to 80° C. by electron beam irradiation under the same conditions is grafted with the temperature-responsive polymer by simultaneously irradiating the surfaces of the materials with electron beams to obtain a temperature-responsive cell culture substrate. According to this method, a temperature-responsive cell culture substrate having a surface (1) that allows cells to adhere thereto and to grow thereon during cell culturing and that allows the adhering and grown cells to be detached therefrom by changing the culturing temperature and a surface (2) that does not allow the cells to adhere thereto at all can be obtained by a simple process.

18 Claims, 4 Drawing Sheets

(56) References Cited

U.S. PATENT DOCUMENTS

| | | |
|---|---|---|
| 2012/0210451 A1 | 8/2012 | Shimizu et al. |
| 2014/0056814 A1 | 2/2014 | Okano et al. |
| 2014/0056858 A1 | 2/2014 | Sugiyama et al. |
| 2014/0056859 A1 | 2/2014 | Okano et al. |
| 2014/0072599 A1 | 3/2014 | Kinooka et al. |
| 2014/0212470 A1 | 7/2014 | Kanzaki et al. |

FOREIGN PATENT DOCUMENTS

| | | |
|---|---|---|
| JP | 02-211865 | 8/1990 |
| JP | 05-192138 | 8/1993 |
| JP | 08-103653 | 4/1996 |
| JP | 3441530 | 9/2003 |
| JP | 3641301 | 1/2005 |
| JP | 2007-014753 | 1/2007 |
| JP | 2008-220320 | 9/2008 |
| JP | 2008-220354 | 9/2008 |
| WO | 01/68799 | 9/2001 |

OTHER PUBLICATIONS

International Search Resort for PCT/JP2009/067774, mailed Nov. 24, 2009.
Supplementary European Search Report for EP 09820595.8, six pages (May 21, 2013).
International Search Report for PCT/JP2009/067774, two pages (Nov. 24, 2009).
Int'l Preliminary Report on Patentability for PCT/JP2009/067774, nine pages (May 17, 2011).

\* cited by examiner

TEMPERATURE-RESPONSIVE CELL CULTURE SUBSTRATE AND METHOD FOR PRODUCING THE SAME

This application the U.S. national stage of International Application No. PCT/JP2009/067774, filed 14 Oct. 2009, which designated the U.S. and claims priority to Application No. JP 2008-288220, filed 14 Oct. 2008; the entire contents of each of which are hereby incorporated by reference.

TECHNICAL FIELD

The present invention relates to a cell culture substrate useful in, for example, biological and medical fields.

BACKGROUND ART

Recently, animal cell culture technology has been remarkably developed, and also research and development targeting animal cells have been carried out over a variety of wide-scale fields. At the first stage of development, animal cells as a target have been used for making products of the cells themselves or making products of materials produced by the cells. Currently, cells and their surface proteins are analyzed to design useful medicines. Furthermore, treatment by growing patients' cells in vitro or enhancing the function of the cells and then returning the cells to the patients' bodies being put into practice. At present, the technology for culturing animal cells is one field to which many researchers pay attention.

Many animal cells including human cells are anchorage-dependent. That is, in order to culture animal cells in vitro, the cells must be once attached to something. Against such background, many researchers have studied or developed substrate surfaces that are more desirable for cells before, but all these technologies are involved in those during cell culture. Cultured anchorage-dependent cells produce adhesive proteins by themselves when they adhere to something. The adhesive proteins must therefore be destroyed usually by enzyme treatment in order to detach the cells in conventional techniques. On such occasion, cell surface proteins that are produced by the cells during the culture and are inherent to various types of cells are also simultaneously destroyed. This severe problem, however, has no actual countermeasure and has not been investigated very often. It is believed that this problem on the collection of cells should be solved for breakthrough in research and development using animal cells in future.

Against such background, JP-A-Hei-2-211865 describes a new method of cell culture including culturing cells on a cell culture support having a substrate surface coated with a polymer having an upper or lower critical solution temperature to water of 0 to 80° C. at a temperature lower than the upper critical solution temperature or not lower than the lower critical solution temperature and then detaching the cultured cells without enzyme treatment by changing the culturing temperature to a temperature of not lower than the upper critical solution temperature or lower than the lower critical solution temperature. JP-A-Hei-5-192138 describes a method of culturing skin cells using this temperature-responsive cell culture substrate at a temperature lower than the upper critical solution temperature or not lower than the lower critical solution temperature and then detaching the cultured skin cells with low damage by changing the culturing temperature to a temperature of not lower than the upper critical solution temperature or lower than the lower critical solution temperature. In addition, Japanese Patent Application No. 2007-105311 describes a method of repairing surface protein of the cultured cells using this temperature-responsive cell culture substrate. The use of the temperature-responsive cell culture substrate contributes to further development of conventional culturing technology.

The conventional culturing technology has been developed in diverse new ways using the temperature-responsive cell culture substrate. However, in this technology, the entire surface of the cell culture substrate is uniformly coated with a temperature-responsive polymer, and the size of the resulting cell sheet always depends on the size of culture substrate. In addition, the cell sheet has a circular shape because the shapes of the culture surfaces of existing culture vessels are usually circular. Accordingly, a disadvantage of the shape is that the cell sheets cannot efficiently arranged on an affected area when they are grafted onto the affected area. Consequently, there is a demand for more precisely designing the temperature-responsive portion of the culture substrate surface.

Regarding the coating state of this temperature-responsive polymer, Japanese Patent No. 3441530 discloses a surface including a region having a specific affinity and a stimulation-responsive polymer region locally in the culturing surface or in a patterned form. However, this method to produce the substrate surface requires at least two steps for forming the respective regions on the same substrate surface and, therefore, is not efficient or simple. Similarly, Japanese Patent No. 3641301 discloses a surface including a region having a specific affinity and a stimulation-responsive polymer region locally in the culturing surface or in a patterned form. In also this technology, the production process of the substrate surface is not simple due to the reasons described above, and there is a demand for developing a new method.

SUMMARY OF INVENTION

Technical Problem

The present invention has been made in order to solve the problems in temperature-responsive cell culture substrates as described above. That is, the present invention provides a novel temperature-responsive cell culture substrate derived from an idea absolutely different from existing technology.

Solution to Problem

The present inventors have researched and developed countermeasures from various angles in order to solve the above-mentioned problems. As a result, it has been found that when a temperature-responsive polymer is tried to be grafted on a substrate surface using electron beams, the graft density of the temperature-responsive polymer varies depending on the material of the substrate even under the same conditions for irradiation with electron beams. The present invention has been made based on this finding, and it has been found that in the case where a cell culture substrate is molded in advance in such a manner that exposed surfaces of two or more materials having different grafting efficiencies for a temperature-responsive polymer by electron beams are flush with each other, it is not necessary to fix the polymer by multiple steps, essential for conventional methods, in the subsequent grafting of the temperature-responsive polymer by electron beam irradiation, and regions having the grafted temperature-responsive polymer in different densities can be produced at the same time by a single electron beam irradiation step. Cells adhere to a surface on which a certain density of temperature-responsive polymer is attached and grown and, then are detached by changing the culturing temperature. It is however known that cells do not adhere to the surface when the density of the temperature-responsive polymer is higher than the certain density. That is, if a large density of the temperature-responsive polymer is grafted in the other region in order to graft a certain density of the temperature-responsive polymer in only a specific region of the substrate surface, cells adhere to only the specific region, grow, and are detached by merely changing the culturing temperature. Furthermore, by making the surface into a specific shape, a cell sheet having a desired shape or size can be obtained. The present invention has been accomplished based on these findings.

The present invention provides a temperature-responsive cell culture substrate comprising a substrate grafted with a temperature-responsive polymer that varies its interaction with water in a temperature range of 0 to 80° C. on a surface having a pattern formed by two or more materials exhibiting different grafting efficiencies for the temperature-responsive polymer by electron beam irradiation under the same conditions, wherein the surfaces of the materials grafted with the temperature-responsive polymer include:

a surface (1) that allows cells to adhere thereto and to grow thereon during cell culturing and that allows the adhering and grown cells to be detached therefrom by changing the culturing temperature; and a surface (2) that does not allow the cells to adhere thereto at all.

Furthermore, the present invention provides a method of producing a temperature-responsive cell culture substrate. The process includes applying a monomer solution to form a temperature-responsive polymer that varies its interaction with water in a temperature range of 0 to 80° C., a polymer solution, or a mixture of the monomer solution and the polymer solution to the entire surface of a substrate, wherein the surface has a pattern formed by two or more materials exhibiting different grafting efficiencies for the temperature-responsive polymer by electron beam irradiation under the same conditions and then irradiating the entire surface of the substrate with the same electron beams to form:

a surface (1) that allows cells to adhere thereto and to grow thereon during cell culturing and that allows the adhering and grown cells to be detached therefrom by changing the culturing temperature; and a surface (2) that does not allow the cells to adhere thereto at all, on the substrate surface.

Advantageous Effects of Invention

According to the substrate described in the present invention, cells adhere to only a region that allows cells to adhere thereto of the substrate surface and can be detached from the region by merely changing the temperature. Accordingly, a cell sheet having a predetermined shape can be obtained. In addition, according to the present invention, regions having different graft densities of the temperature-responsive polymer can be simultaneously produced by a single electron beam irradiation step.

DESCRIPTION OF EMBODIMENTS

In this application, the term "grafting" refers to fixation (binding) of a temperature-responsive polymer that varies its interaction with water in a temperature range of 0 to 80° C. to the surface of a culturing substrate. In this application, the term "fixation" has the same meaning as that of "grafting". The density thereof is expressed as weight per unit area, "$\mu g/cm^2$", in this application, as shown below, but is not limited thereto.

In the application, the term "grafting efficiency" refers to the degree of "fixation" or "grafting" of a temperature-responsive polymer that varies its interaction with water in a temperature range of 0 to 80° C. to a substrate surface. That is, if a temperature-responsive polymer that varies its interaction with water in a temperature range of 0 to 80° C. is fixed in a larger density to a specific substrate surface among substrate surfaces composed of different materials under the same conditions, the specific substrate surface is a material having a high grafting efficiency.

The present invention provides a novel temperature-responsive cell culture substrate. This substrate has a specific surface to which a temperature-responsive polymer is grafted. The cell culture substrate having the specific surface is an exposed surface composed of two or more materials exhibiting different grafting efficiencies for the temperature-responsive polymer that varies its interaction with water in a temperature range of 0 to 80° C. by electron beam irradiation under the same conditions. That is, a temperature-responsive cell culture substrate of the present invention must include a surface (1) that allows cells to adhere thereto and to grow thereon during cell culturing and that allows the adhering and grown cells to be detached therefrom by changing the culturing temperature (hereinafter referred to as "cell adhering surface (1)") and a surface (2) that does not allow the cells to adhere thereto at all (hereinafter referred to as "cell non-adhering surface (2)") after grafting of the temperature-responsive polymer. On this occasion, the materials having different grafting efficiencies are not particularly limited, but the former, the cell adhering surface (1), is any of polystyrene, polycarbonate, and polymethyl methacrylate, or a combination of two or more thereof. Among them, particularly preferred is commonly used polystyrene as a substrate for cell culture.

In the present invention, a surface that becomes the cell non-adhering surface (2) after it is irradiated with electron beams under the same conditions as those for irradiation to the cell adhering surface (1) is necessary. Such a material is not particularly limited as long as the temperature-responsive polymer is grafted to the material in a density that does not allow cells to adhere to the temperature-responsive polymer by irradiation with electron beams under the same conditions as those for irradiation with electron beams to the material of the cell adhering surface (1) that is any of polystyrene, polycarbonate, and polymethyl methacrylate or a combination of two or more thereof. Examples of such a material include polymethylpentene, polyethylene terephthalate, polyethylene, polypropylene, an ABS resin, polyoxymethylene, nylon, and polytetrafluoroethylene. Among them, preferred is polymethylpentene compatible with any of polystyrene, polycarbonate, and polymethyl methacrylate or a combination of two or more thereof as the material of the cell adhering surface (1) during molding the substrate.

As described above, the present invention utilizes a substrate having a surface on which materials exhibiting different grafting efficiencies for a temperature-responsive polymer by electron beam irradiation are exposed. The specific examples of the material of the cell adhering surface (1) and the specific examples of the material of the cell non-adhering surface (2) on which the temperature-responsive polymer is grafted at a density not to allow cells to adhere thereto by being irradiated with electron beams under the same conditions as those for obtaining the cell adhering surface (1) have been exemplified. However, the material used as the cell non-adhering surface (2), such as polymethylpentene and polyethylene terephthalate, can provide a surface that allows cells to adhere thereto and to grow thereon during cell culturing and that allows the adhering and grown cells to be detached therefrom by changing the culturing temperature by grafting the temperature-responsive polymer through irradiation with electron beams under optimized conditions. Accordingly, in the present invention, the material of the cell non-adhering surface (2) is determined according to the material of the cell adhering surface (1). For example, if the material of the cell adhering surface (1) is polymethylpentene or polyethylene terephthalate, the material of the cell non-adhering surface (2) is polytetrafluoroethylene. The present invention is directed to graft a temperature-responsive polymer on a single cell culture surface composed of different materials by electron beam treatment at a single time in different densities for regions of the respective materials. The conditions of electron beam irradiation, such as dose, intensity, time, and acceleration voltage, are not particularly limited and may be those for common irradiation. The material of the temperature-responsive polymer to be grafted may be a monomer thereof or the polymer itself or a mixture of the monomer and the polymer. The material may be applied to the substrate surface in a solution or solid form or in a form of a mixture of the solution and the solid. The state of the material is not particularly limited in the present invention.

In the present invention, the proportion between the cell adhering surface (1) and the cell non-adhering surface (2) is not particularly limited, and, for example, the culture substrate surface may be composed of a cell non-adhering surface (2) surrounding a cell adhering surface (1), or the reversal positional relationship, i.e., a cell adhering surface (1) surrounding a cell non-adhering surface (2). Alternatively, the substrate surface may have a plurality of regions of the cell adhering surface (1) and/or the cell non-adhering surface (2). The shape of the surface of each material is also not particularly limited, but polygonal cell sheets obtained from the cell adhering surface (1) can be favorably transplanted at a plurality of sites without overlapping. Specific examples include triangular, quadrangular, tetragonal, and hexagonal cell sheets. Among them, a quadrangular cell sheet, which is easy to handle, is preferred. In addition, in the present invention, the following fact has been also found: The contoured part of each shape is a boundary of regions where the temperature-responsive polymer is grafted in different densities. In one region separated by the boundary, cells have grown into a sheet form and adhere to the substrate surface, while in the other region, cells do not adhere thereto at all. Such a boundary can effectively work as a starting point for easily detaching the cultured cells in a sheet form.

The present invention utilizes a temperature-responsive polymer having variable hydration ability in a temperature range of 0 to 80° C. In the present invention, the temperature-responsive cell culture substrate as an object has a surface coated with the polymer having variable hydration ability in a temperature range of 0 to 80° C. The temperature-responsive polymer used in the present invention may be either a homopolymer or a copolymer. Examples of these polymers are described in JP-A-Hei-2-211865. Specifically, for example, a polymer can be prepared by homopolymerization or copolymerization of the following monomers. Examples of the usable monomer include (meth)acrylamide compounds, N-(or N,N-di-)alkyl-substituted (meth)acrylamide derivatives, and vinyl ether derivatives. In the case of a copolymer, any two or more of the above monomers can be used. Furthermore, monomers other than the above-mentioned monomers, copolymers with ionic monomers for improving adhesion and growth of cells, graft polymers or copolymers of polymers, and mixtures of polymers and copolymers can be used. In addition, the polymers can be cross-linked in the range that does not impair the inherent properties.

In the present invention, the density of the temperature-responsive polymer fixed in the cell adhering surface (1) is not particularly limited as long as it is fixed in a sufficient density for culturing cells and detaching the cultured cells from the substrate surface merely by a temperature operation, but is 0.7 to 2.5 $\mu g/cm^2$, preferably 1.3 to 2.3 $\mu g/cm^2$, more preferably 1.5 to 2.1 $\mu g/cm^2$, and most preferably 1.8 to 2.0 $\mu g/cm^2$. A polymer density of larger than 2.5 $\mu g/cm^2$ decreases the adhesion of cells, and a density of smaller than 0.7 $\mu g/cm^2$ does not cause detachment even if the temperature is changed, which does not cause a significant difference from the cell non-adhering surface (2) and disadvantageously prevents the technology of the present invention from being sufficiently achieved. The density of a fixed polymer may be measured by a common process, for example, either a direct measurement by FT-IR-ATR or estimation based on the density of a labeled polymer labeled in advance and fixed by the same process.

In the present invention, the density of the temperature-responsive polymer fixed in the cell non-adhering surface (2) is not particularly limited as long as it is fixed in a sufficient density to inhibit cells from adhering thereto, but is 2.7 $\mu g/cm^2$ or more, preferably 3.0 $\mu g/cm^2$ or more, more preferably 3.5 $\mu g/cm^2$ or more, and most preferably 4.0 $\mu g/cm^2$ or more. In a polymer density of smaller than 2.7 $\mu g/cm^2$, a significant difference cannot be found between the cell adhering surface (1) and the cell non-adhering surface (2), which disadvantageously prevents the technology of the present invention from being achieved.

The shape of the culture substrate in the present invention is not particularly limited, and examples thereof include dish, multi-plate, flask, and cell-insert shapes.

In the cell culture support of the present invention, the temperature-responsive polymer coated on the substrate causes hydration or dehydration by changing the temperature, and it was revealed that the temperature range is 0 to 80° C., preferably 10 to 50° C., and more preferably 20 to 45° C. A temperature higher than 80° C. may cause disadvantageous death of cells, and a temperature lower than 0°

C. generally disadvantageously causes a significant decrease in cell-growth rate or causes death of cells.

The present invention utilizes a substrate having a surface on which materials exhibiting different grafting efficiencies for a temperature-responsive polymer by electron beam irradiation are exposed. Such a substrate may be formed by any method without particular limitation. Examples of the method include insert molding and coinjection molding, and they are properly used according to the shape and size of the product, and the material to be used for the molding.

In the present invention, a temperature-responsive polymer is grafted using electron beams on a substrate surface on which materials exhibiting different grafting efficiencies for the temperature-responsive polymer by electron beam irradiation are exposed. Since one object of the present invention is to simplify the electron beam irradiation procedure, a smaller number of cycles of the electron beam irradiation are preferred. The method thereof is not particularly limited, and, for example, in a preferred method, a monomer solution to form a temperature-responsive polymer or a polymer solution or a mixture thereof is applied to the entire surface of a substrate that has been patterned by two or more materials exhibiting different grafting efficiencies for the temperature-responsive polymer that varies its interaction with water in a temperature range of 0 to 80° C., and then the entire surface of the substrate is irradiated with electron beams at a single time.

The temperature-responsive cell culture substrate of the present invention can be used for, but not limited to, various cells, for example, animal, insect, and plant cells and bacteria. Among them, preferred are animal cells many of which are commercially available. Animal cells are derived from, for example, human, monkey, dog, cat, rabbit, rat, nude mouse, mouse, guinea pig, hog, sheep, Chinese hamster, bovine, marmoset, or African green monkey, but are not particularly limited. Particularly preferred cells in the present invention are established cell lines of animal cells, which can be stably cultured. Examples of the cell lines include, but not limited to, an NIH/3T3 cell line (mouse embryonic fibroblast), 3T3-Swiss albino cell line (mouse embryonic fibroblast), A549 cell line (human lung carcinoma cell), HeLa cell line (human cervical carcinoma cell), Vero cell line (normal African green monkey kidney cell), 293 (human fetal kidney cell), 3T3-L1 (mouse fibroblast), HepG2 (human hepatocellular liver carcinoma cell), MCF-7 (human breast cancer cell), V79 (Chinese hamster fibroblast), COS-7 (African green monkey kidney cell), CHO-K1 (Chinese hamster ovary cell), WI-38 (human lung fibroblast), MDCK (dog kidney cell), and MRC-5 (normal human lung fibroblast). The number of seeding cells, culturing time, and medium for culturing the cells may be usual conditions without any limitation.

The terms outlined above will be explained by poly(N-isopropylacrylamide) as an example of the temperature-responsive polymer. The temperature-responsive cell culture substrate of the present invention has a surface including a surface (1) that allows cells to adhere thereto and to grow thereon during cell culturing and that allows the adhering and grown cells to be detached therefrom by changing the culturing temperature and a surface (2) that does not allow the cells to adhere thereto at all. On both surfaces, poly(N-isopropylacrylamide) is grafted. Poly(N-isopropylacrylamide) is known as a polymer having a lower critical solution temperature of 31° C. and causes dehydration in water at a temperature of 31° C. or higher if it is a free state to aggregate the polymer chains to cause white turbidity. On the contrary, at a temperature of lower than 31° C., the polymer chains are hydrated into a water-dissolved state. In the substrate as an object of the present invention, this polymer is fixed to the surface of a substrate such as a petri dish. In the surface (1) that allows cells to adhere thereto and to grow thereon during cell culturing and that allows the adhering and grown cells to be detached therefrom by changing the culturing temperature, the polymer on the substrate surface is similarly dehydrated at a temperature of 31° C. or higher, and since the polymer chain covers the substrate surface and is fixed thereto, the substrate surface shows hydrophobicity. Conversely, at a temperature lower than 31° C., the polymer on the substrate surface is hydrated, while the polymer chain covers the substrate surface and is fixed thereto; thus, the substrate surface shows hydrophilicity. The hydrophobic surface is a surface suitable for adhesion and growth of cells, while the hydrophilic surface is a surface to which cells cannot adhere. Accordingly, cells during culturing can be detached by merely cooling. Meanwhile, in the surface (2) that does not allow cells to adhere thereto at all, since the grafted density of poly(N-isopropylacrylamide) is too high, cells do not adhere thereto at all. That is, cells adhere to and to grow in a predetermined region only, and the cells can be detached by changing the culturing temperature.

According to the present invention, cells can adhere to and to grow on only a predetermined surface region of the temperature-responsive cell culture substrate, and the cultured cells can be detached by changing the culturing temperature. According to the method of the present invention, such a substrate can be easily produced, which contributes to propagation of a cell culture technology using the temperature-responsive cell culture substrate.

EXAMPLES

The present invention will be described in further detail below based on examples, but should not be limited to these examples.

Example 1

Figure 1:
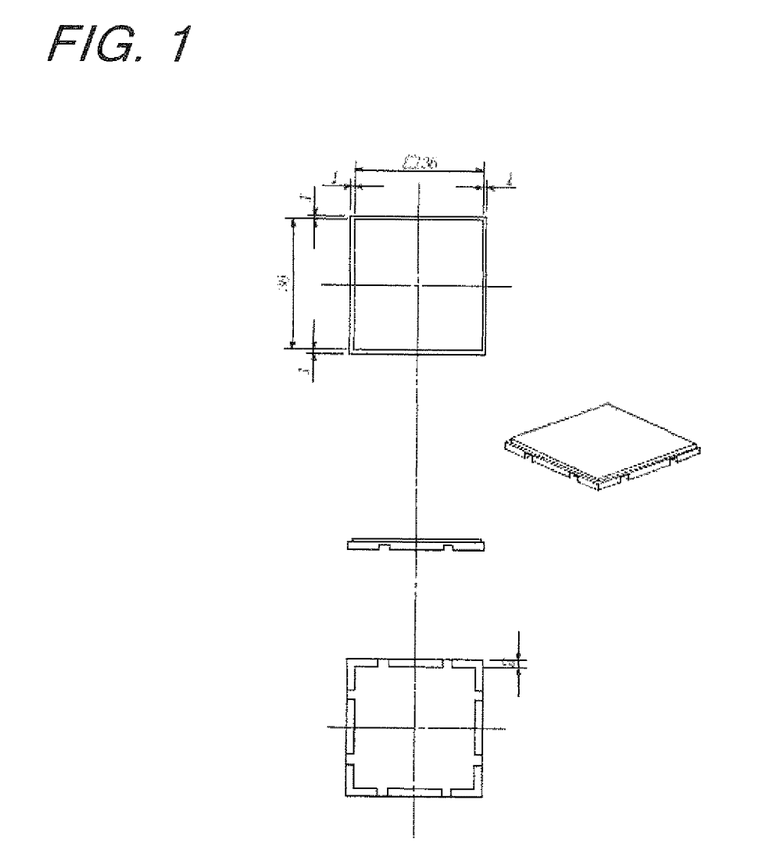
FIG. 1 is a diagram illustrating the shape of a polystyrene portion of Example 1.
Figure 2:
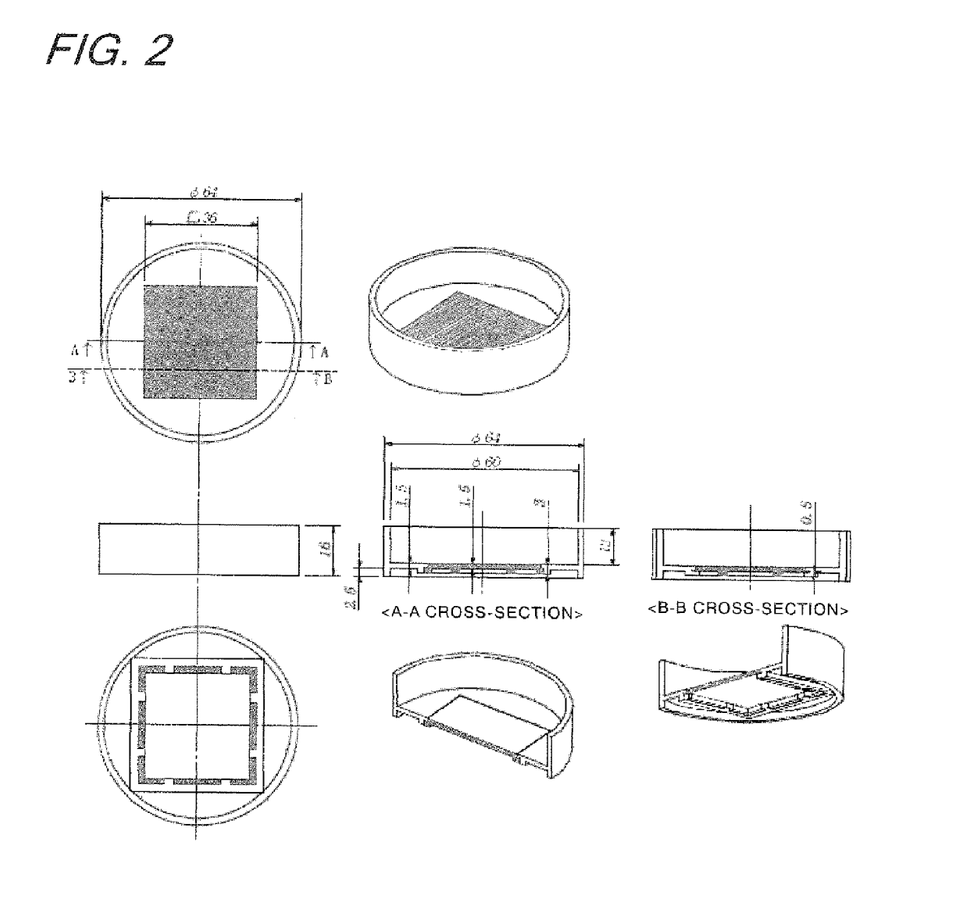
FIG. 2 is a diagram illustrating an entire basal dish of a temperature-responsive cell culture substrate of Example 1.
Figure 3:
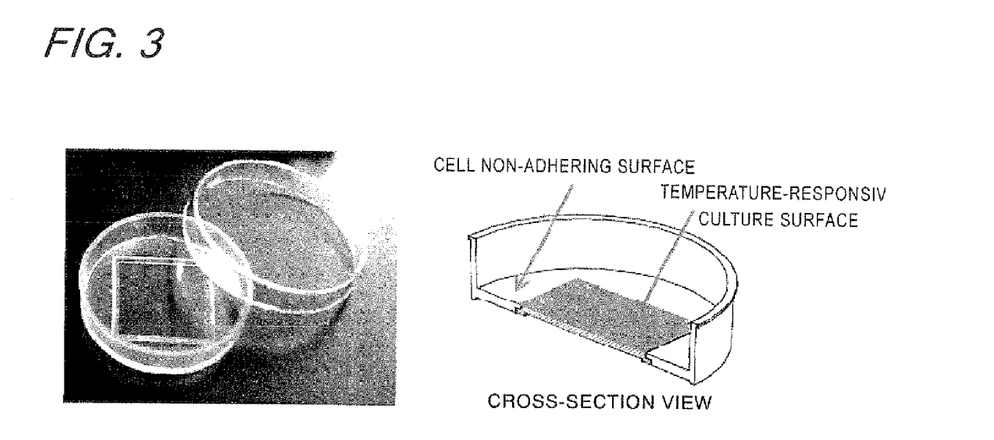
FIG. 3 is a diagram illustrating an entire basal dish of a temperature-responsive cell culture substrate obtained in Example 1.

Poly-N-isopropylacrylamide was selected as a temperature-responsive polymer, and a polystyrene resin was selected as a material that was grafted by the polymer to form a surface that allows cells to adhere thereto and to grow thereon during cell culturing and that allows the adhering and grown cells to be detached therefrom by changing the culturing temperature. First, the polystyrene surface was molded. FIG. 1 shows a design of the molded product. The injection molding was carried out under the following conditions: a cylinder temperature of 200° C., an injection pressure of 400 kg/cm$^2$, an injection rate of 10/100 mm/sec, a cooling time of 20 sec, and a die temperature of 50° C. The injection molding machine used was a model M-100 manufactured by Meiki Co., Ltd. Then, this flat polystyrene plate was placed in the model M-100 manufactured by Meiki Co., Ltd. and was injection-molded into a polymethylpentene to form a polymethylpentene dish having a quadrangular polystyrene surface. FIG. 2 shows a design of the molded product. The black quadrangular portion in FIG. 2 corresponds to the polystyrene surface. The injection molding was carried out under the following conditions: a cylinder temperature of 300° C., an injection pressure of 470 kg/cm$^2$, an injection rate of 10/100 mm/sec, a cooling time of 23 sec, and a die temperature of 55° C. The resulting molded product is shown in FIG. 3. The drawing shown in the right of FIG. 3 is a schematic view of a cross section cut with a straight line passing through the central portion of the molded product. It shows the assembly of the polystyrene portion and the polymethylpentene portion. A basal dish of an inventive temperature-responsive cell culture substrate was produced using polystyrene and polymethylpentene.

Then, a temperature-responsive polymer was grafted on this basal dish using electron beams. Onto the basal dish, 0.07 mL of isopropyl alcohol containing 52% N-isopropylacrylamide monomer was applied. The entire surface of the basal dish was irradiated with electron beams at a dose of 0.25 MGy for fixing poly-N-isopropylacrylamide (PIPAAm) on the surface of the basal dish. After the irradiation, the basal dish surface was washed with deionized water to remove the remaining monomer and PIPAAm not bound to the basal dish, followed by drying in a clean bench and sterilization with gaseous ethylene oxide. Thus, a temperature-responsive cell culture substrate was obtained. The density of the temperature-responsive polymer grafted on the substrate surface was measured. The polystyrene surface was coated at a density of 1.9 µg/cm$^2$ and the polymethylpentene surface was coated at a density of 3.0 µg/cm$^2$. Through the procedure described above, a temperature-responsive cell culture substrate of the present invention was produced.

Figure 4:
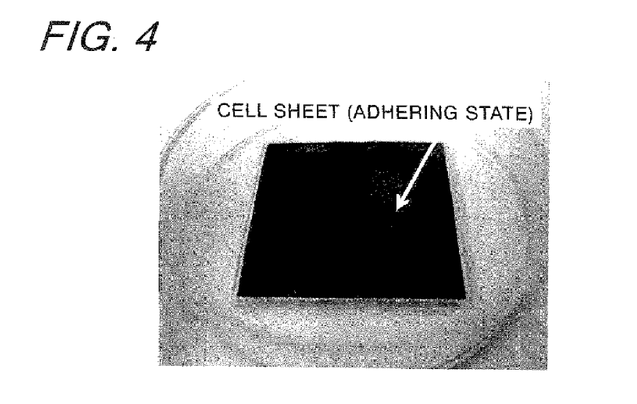
FIG. 4 is a diagram illustrating the results of culturing human skeletal muscle myoblast in Example 1, wherein the cultured cells are stained for convenience of observation.
Figure 5:
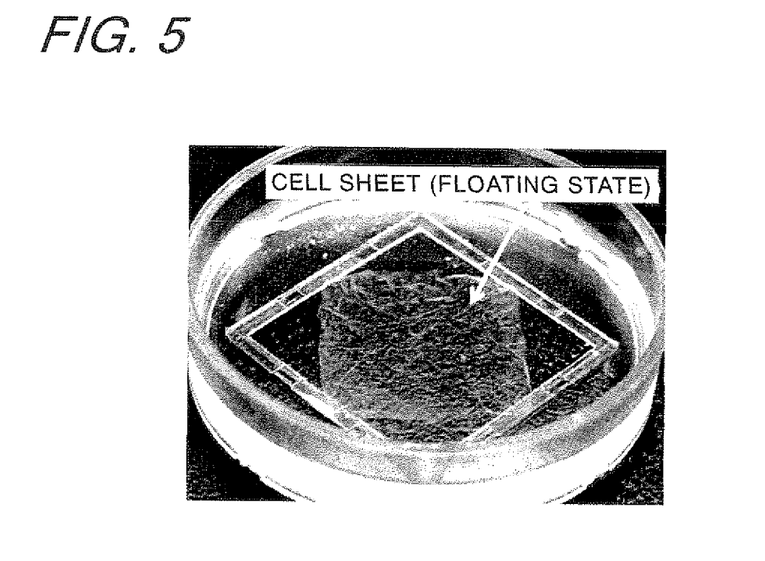
FIG. 5 is a diagram illustrating cultured cells after cooling in Example 1.

This substrate surface was immersed with 8 mL of a cell culture solution (ABM basal medium containing 10% bovine fetal serum, EGF, dexamethasone sodium phosphate, gentamicin sulfate, and amphotericin B in a usual manner) kept at 37° C. The substrate was placed in a carbon dioxide culture apparatus at 37° C. for 15 minutes. Then, 1×10$^5$ cells/cm$^2$ of human skeletal muscle myoblasts were seeded on another substrate surface at a cell density range where the cells do not come in contact with one another and were cultured at 37° C. under an atmosphere of 5% carbon dioxide gas in a carbon dioxide culture apparatus for four days. FIG. 4 shows the appearance after the culturing. In FIG. 4, the cultured cells were stained in blue for easy observation. It can be confirmed that the cultured human skeletal muscle myoblasts become confluent to form a sheet-like shape. The temperature-responsive cell culture substrate was taken out from the carbon dioxide culture apparatus, and the human skeletal muscle myoblasts obtained in the sheet-like shape were detached from the substrate surface by leaving the substrate to stand at 20° C. for 15 minutes. FIG. 5 shows the results. Accordingly, a temperature-responsive cell culture substrate of the present invention can be obtained and that a cultured cell sheet having a desired shape and size can also be obtained by culturing cells using this substrate.

Comparative Example 1

To the basal dish of the temperature-responsive cell culture substrate prepared in Example 1 was applied 0.07 mL of isopropyl alcohol containing 35% N-isopropylacrylamide monomer. The entire surface of the basal dish was irradiated with electron beams at a dose of 0.25 MGy for fixing poly-N-isopropylacrylamide (PIPAAm) on the surface of the basal dish. After the irradiation, the basal dish surface was washed with deionized water to remove the remaining monomer and PIPAAm not bound to the basal dish, followed by drying in a clean bench and sterilization with gaseous ethylene oxide. Thus, a temperature-responsive cell culture substrate was obtained. The density of the temperature-responsive polymer grafted on the substrate surface was measured to confirm that the polystyrene surface was coated at a density of 1.3 µg/cm$^2$ and the polymethylpentene surface was coated at a density of 2.4 µg/cm$^2$. Human skeletal muscle myoblasts were seeded on this substrate and were cultured as in Example 1. As a result, the cells on the polystyrene portion of the temperature-responsive cell culture substrate surface grew to a confluent state, and the cells on the polymethylpentene portion at the circumference thereof also grew. As in Example 1, the temperature-responsive cell culture substrate was cooled, but the cells on the entire surface of the temperature-responsive cell culture substrate were detached not to give a quadrangular cell sheet.

Example 2

Figure 6:
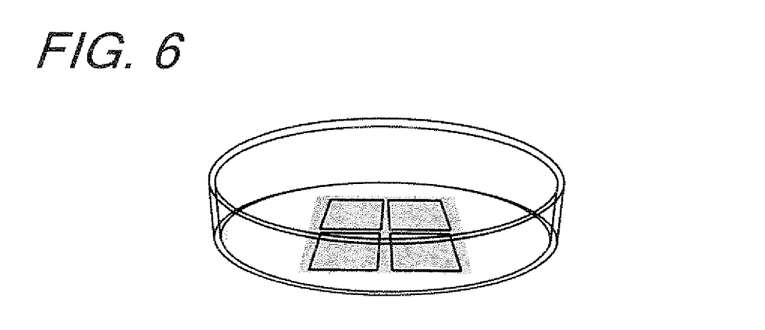
FIG. 6 is a diagram illustrating an entire basal dish of a temperature-responsive cell culture substrate of Example 2.

Poly-N-isopropylacrylamide was selected as a temperature-responsive polymer, and a polystyrene resin was selected as a material that was grafted by the polymer to form a surface that allows cells to adhere thereto and to grow thereon during cell culturing and that allows the adhering and grown cells to be detached therefrom by changing the culturing temperature, as in Example 1. The polystyrene surface was molded into a shape shown in FIG. 6. First, a quadrangular polystyrene plate was produced under the following injection conditions: a cylinder temperature of 200° C., an injection pressure of 400 kg/cm$^2$, an injection rate of 10/100 mm/sec, a cooling time of 20 sec, and a die temperature of 50° C. (one black portion at the center of FIG. 6), as in Example 1. The injection molding machine used was a model M-100 manufactured by Meiki Co., Ltd., as in Example 1. Then, this flat polystyrene plate was placed in the model M-100 manufactured by Meiki Co., Ltd. and was injection-molded into a polymethylpentene to form a polymethylpentene dish having a quadrangular polystyrene surface. On this occasion, the molding was performed in such a manner that only a part of the polystyrene plate is exposed (four quadrangular portions in FIG. 6) and other portion is coated with polymethylpentene. Four quadrangular portions in FIG. 6 correspond to the polystyrene surfaces. The injection molding was carried out by the following conditions: a cylinder temperature of 300° C., an injection pressure of 470 kg/cm$^2$, an injection rate of 10/100 mm/sec, a cooling time of 23 sec, and a die temperature of 55° C. A basal dish of the temperature-responsive cell culture substrate of the present invention was produced using polystyrene and polymethylpentene. Then, a temperature-responsive polymer was grafted on this basal dish using electron beams. Onto the basal dish was applied 0.07 mL of isopropyl alcohol containing 54% N-isopropylacrylamide monomer. The entire surface of the basal dish was irradiated with electron beams at a dose of 0.25 MGy for fixing poly-N-isopropylacrylamide (PIPAAm) on the surface of the basal dish. After the irradiation, the basal dish surface was washed with deionized water to remove the remaining monomer and PIPAAm not bound to the basal dish, followed by drying in a clean bench and sterilization with gaseous ethylene oxide. Thus, a temperature-responsive cell culture substrate was obtained. The density of the temperature-responsive polymer grafted on the substrate surface was measured to confirm that the polystyrene surface was coated at a density of 2.0 µg/cm$^2$ and the polymethylpentene surface was coated at a density of 3.1 µg/cm$^2$. Through the procedure described above, a temperature-responsive cell culture substrate of the present invention was produced. Human skeletal muscle myoblasts were cultured as in Example 1 for four days and were cooled as in Example 1 to detach cell sheets from the four quadrangular portions shown in FIG. 6. Accordingly, it was confirmed that the temperature-responsive cell culture substrate of the present invention can be obtained and that cultured cell sheets having desired shapes and sizes can be obtained by culturing cells using this substrate.

Example 3

Figure 7:
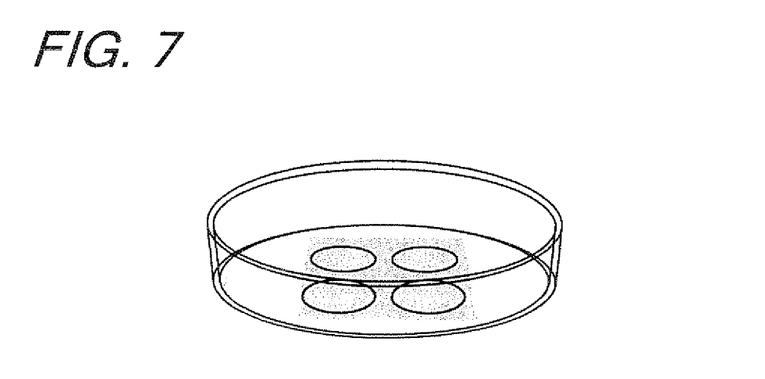
FIG. 7 is a diagram illustrating an entire basal dish of a temperature-responsive cell culture substrate of Example 3.

Investigation was performed as in Example 2 except that exposure portions of the polystyrene surface were four circular portions as shown in the center of FIG. 7. Human skeletal muscle myoblasts were cultured by the procedure as in Example 1 for four days and were cooled as in Example 1 to detach cell sheets from the four circular portions shown in FIG. 7. This confirmed that the temperature-responsive cell culture substrate of the present invention can be obtained and that cultured cell sheets having desired shapes and sizes can be obtained by culturing cells using this substrate.

INDUSTRIAL APPLICABILITY

Using a substrate described in the present invention, cells adhere to and grow on only a region of the substrate surface where cells can adhere to, and a cell sheet having specific shape and size can be obtained. The cultured cell sheet obtained by this method is highly expected to be used for clinical applications such as corneal transplant, skin transplant, corneal disease treatment, and ischemic heart disease treatment. The present invention can produce such a substrate by a single electron beam irradiation operation. Accordingly, the present invention is significantly useful in the medical and biological fields, such as cellular engineering and medical engineering.

The invention claimed is:

1. A temperature-responsive cell culture substrate comprising: a substrate grafted with a temperature-responsive polymer that varies its interaction with water in a temperature range of 0 to 80° C. on a surface having two or more portions, wherein the two or more portions are comprised of different materials exhibiting different grafting efficiencies for the temperature-responsive polymer by electron beam irradiation under the same conditions, wherein the two or more portions comprise:
   a portion (1) that allows cells to adhere thereto and to grow thereon during cell culturing and that allows the adhering and grown cells to be detached therefrom by changing the culturing temperature, and
   a portion (2) that does not allow the cells to adhere thereto at all;
   wherein the material of the portion (1) is any one selected from the group consisting of polystyrene, polycarbonate, and polymethyl methacrylate or a combination of two or more thereof; and the material of the portion (2) is any one selected from the group consisting of polymethylpentene, polyethylene terephthalate, polyethylene, polypropylene, and an ABS resin or a combination of two or more thereof.

2. The temperature-responsive cell culture substrate according to claim 1, wherein the portion (2) surrounds a single portion (1).

3. The temperature-responsive cell culture substrate according to claim 2, wherein the portion (1) has a quadrangular shape.

4. The temperature-responsive cell culture substrate according to claim 1, wherein the temperature-responsive polymer is poly-N-isopropylacrylamide.

5. The temperature-responsive cell culture substrate according to claim 4, wherein the temperature-responsive polymer is copolymerized with an ionic monomer component.

6. The temperature-responsive cell culture substrate according to claim 1, wherein the density of the temperature-responsive polymer grafted to the portion (1) is 0.7 to 2.5 $\mu g/cm^2$.

7. The temperature-responsive cell culture substrate according to claim 6, wherein the density of the temperature-responsive polymer grafted to the portion (2) is 2.7 $\mu g/cm^2$ or more.

8. The temperature-responsive cell culture substrate according to claim 1, wherein the density of the temperature-responsive polymer grafted to the portion (2) is 2.7 $\mu g/cm^2$ or more.

9. The temperature-responsive cell culture substrate according to claim 1, wherein the substrate having a surface that is patterned by two or more portions is formed by either coinjection molding or insert molding; wherein the material of the portion (1) is any one of the group consisting of polystyrene, polycarbonate and polymethyl methacrylate or a combination of two or more thereof, while the material of the portion (2) is any one of the group consisting of polymethylpentene, polyethylene terephthalate, polyethylene, polypropylene, and an ABS resin or a combination of two or more thereof.

10. A method of producing a temperature-responsive cell culture substrate, the process comprising applying a solution of a monomer to form a temperature-responsive polymer that varies its interaction with water in a temperature range of 0 to 80° C. or a solution of the polymer or a mixture of the monomer and the polymer to the entire surface of a substrate, wherein the surface has two or more portions, wherein the two or more portions are comprised of different materials exhibiting different grafting efficiencies for the temperature-responsive polymer by electron beam irradiation under the same conditions, and then irradiating the entire surface of the substrate with the same electron beams to form:
   a portion (1) that allows cells to adhere thereto and to grow thereon during cell culturing and that allows the adhering and grown cells to be detached therefrom by changing the culturing temperature, and
   a portion (2) that does not allow the cells to adhere thereto at all, on the substrate surface; wherein the material of the portion (1) is any one selected from the group consisting of polystyrene, polycarbonate, and polymethyl methacrylate or a combination of two or more thereof; and the material of the portion (2) is any one selected from the group consisting of polymethylpentene, polyethylene terephthalate, polyethylene, polypropylene, and an ABS resin or a combination of two or more thereof.

11. The method of producing a temperature-responsive cell culture substrate according to claim 10, wherein the portion (2) surrounds a single portion (1).

12. The method of producing a temperature-responsive cell culture substrate according to claim 11, wherein the portion (1) has a quadrangular shape.

13. The method of producing a temperature-responsive cell culture substrate according to claim 10, wherein the temperature-responsive polymer is poly-N-isopropylacrylamide.

14. The method of producing a temperature-responsive cell culture substrate according to claim 13, wherein the temperature-responsive polymer is copolymerized with an ionic monomer component.

15. The method of producing a temperature-responsive cell culture substrate according to claim 10, wherein the density of the temperature-responsive polymer grafted to the portion (1) is 0.7 to 2.5 µg/cm$^2$.

16. The method of producing a temperature-responsive cell culture according to claim 15, wherein the density of the temperature-responsive polymer grafted to the portion (2) is 2.7 µg/cm$^2$ or more.

17. The method of producing a temperature-responsive cell culture substrate according to claim 10, wherein the density of the temperature-responsive polymer grafted to the portion (2) is 2.7 µg/cm$^2$ or more.

18. The method of producing a temperature-responsive cell culture substrate according to claim 10, wherein the substrate having a surface that is patterned by two or more portions is formed by either coinjection molding or insert molding; wherein the material of the portion (1) is any one of the group consisting of polystyrene, polycarbonate, and polymethyl methacrylate or a combination of two or more thereof, while the material of the portion (2) is any one of the group consisting of polymethylpentene, polyethylene terephthalate, polyethylene, polypropylene, and an ABS resin or a combination of two or more thereof.

* * * * *